CHRYSANTHEMUM PLANT
Filed Aug. 4, 1972 2 Sheets-Sheet 1
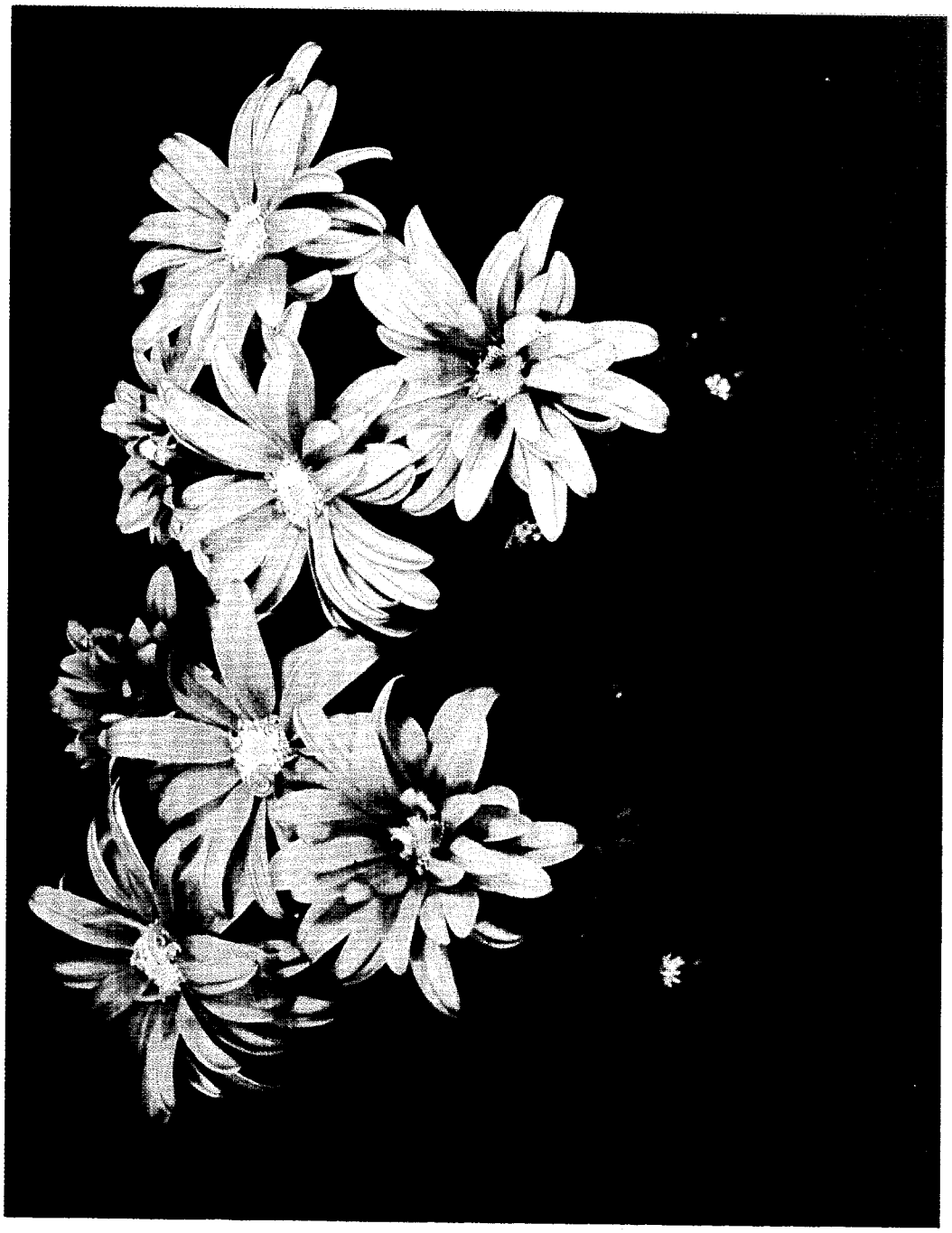

CHRYSANTHEMUM PLANT
Filed Aug. 4, 1972 2 Sheets-Sheet 2
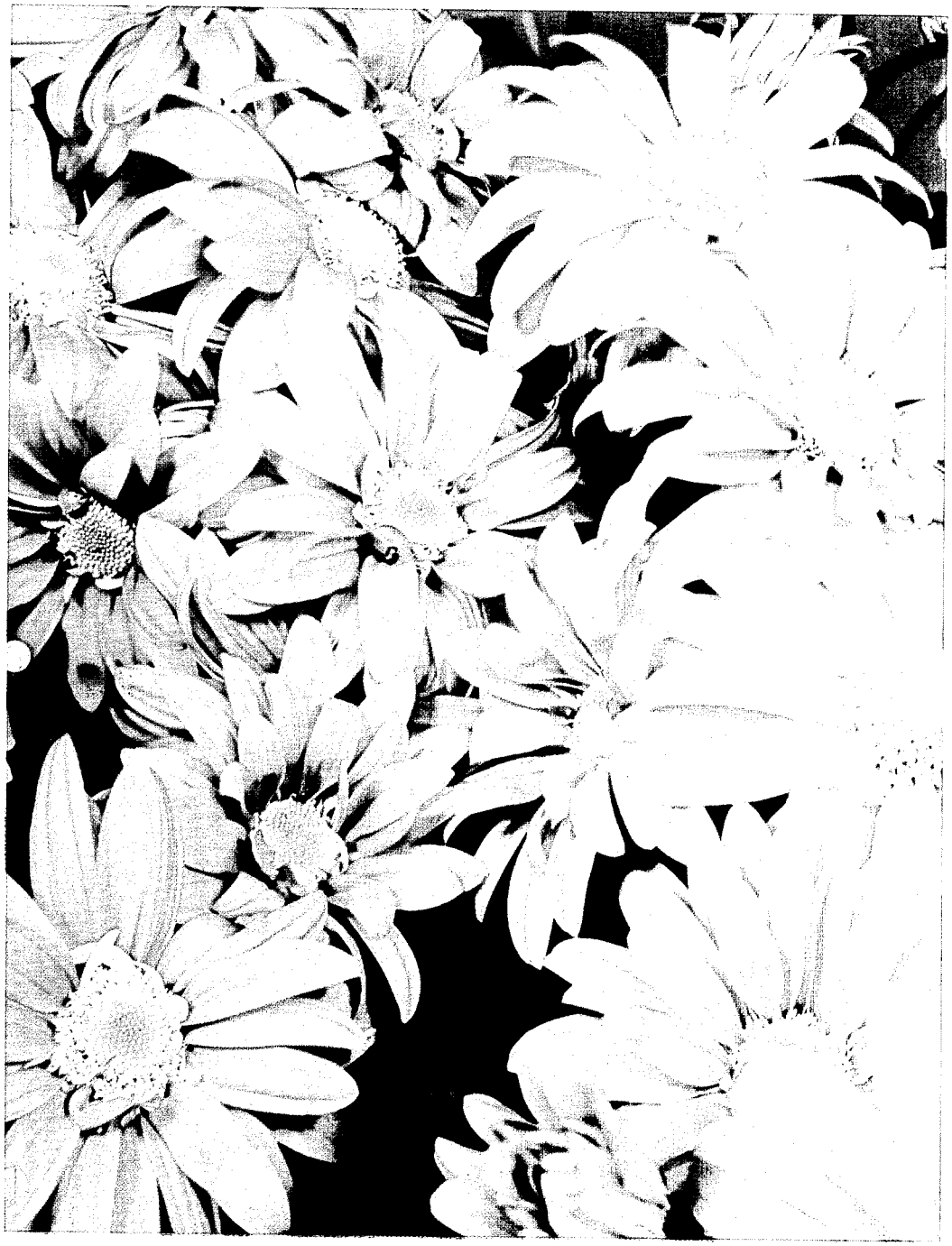

United States Patent Office

Plant Pat. 3,523

Patented Mar. 19, 1974

3,523
CHRYSANTHEMUM PLANT

Ralph Bond, 647 Camellia Drive, Fort Myers, Fla. 33902, and Walter H. Jessel, Jr., Doylestown, and William E. Duffett, Akron, Ohio; said Jessel and Duffett assignors to said Bond

Filed Aug. 4, 1972, Ser. No. 277,866

Int. Cl. A01h *5/00*

U.S. Cl. Plt.—74 1 Claim

The present invention comprises a new and distinct cultivar of chrysanthemum plant identified by the varietal name Red Dazzler, and is a sport of the unpatented cultivar known in the United States as Dazzler.

The new cultivar is similar in many respects to Dazzler, having the same characteristics of:

(1) Plant habit.
(2) Flower size.
(3) Daisy flower form.
(4) Flowering response.

The new cultivar is distinguished from Dazzler by its darker, more intense red-bronze flower color, which provides less fading and a darker but more lively red-bronze color under high light, high temperature conditions. The intense red-bronze color under the noted conditions also distinguishes the new cultivar from other bronze daisies in the floriculture industry.

The new cultivar was discovered in the form of two flowered plants at Fort Myers, Fla., and when asexually reproduced by cuttings at Barberton, Ohio, has been found to retain its distinctive characteristics through successive propagations.

The new cultivar when grown in the vicinity of Barberton, Ohio, has a response period of approximately nine weeks, and the following detailed description is based on observations made of the new cultivar in a greenhouse in Barberton, Ohio. The response time, blooming period, color and total vigor may vary significantly with varying environmental conditions such as temperature, day length and light intensity.

Suggested flowering in the northern and western United States is from April through October; coastal California, April through October; Florida, December through April.

In the accompanying color photographic drawings, Sheet 1 is a comparison photograph, with the new cultivar appearing on the left and the parent cultivar Dazzler on the right. Sheet 2 is a close-up comparison photograph, with the new cultivar again appearing on the left and the cultivar Dazzler on the right. The distinctive red-bronze flower color of the new cultivar is particularly evident in Sheet 2 of the drawings.

In the following description, color references are to the Munsell Color Book, 1963 edition, and comparisons in color values are made with the parent cultivar Dazzler.

Botanical Classification: *Chrysanthemum morifolium*

| | Red Dazzler | Dazzler |
|---|---|---|
| Bloom: | | |
| Size | 3¼″ | |
| Fully expanded | 3¾″ | |
| Borne | Clusters on elongated pedicels | |
| Stems | Strong and wiry | |
| Permanence | 7–10 days | |
| Form | Daisy (single) | |
| Color: | | |
| Center of flower | Yellow green 2.5GY5/8 to yellow 3.75Y8/12 | Yellow green 2.5GY5/8 to yellow 3.75Y8/12. |
| Base of petals | Yellow 5Y8.5/12 | Yellow 5Y8.5/12. |
| Inside of petals | Red 8.75R4/14 over amber 10YR6/8 to bronze 1.25YR4/2 over amber 10YR6/8. | Red, 8.75R4/14 to orange bronze, 2.5YR5/10. |
| Reverse of petals | Bronze 1.25YR4/12 over amber 10YR6/8 | Yellow bronze 10YR6/8 streaked orange bronze 2.5YR5/10. |
| Tonality from a distance | Red bronze | Orange bronze. |
| Discoloration | Bronze 1.25YR4/12 over amber 10YR6/8 | Orange bronze 2.5YR5/10. |
| Petals: | | |
| Texture | Smooth | |
| Appearance & form | Open at base, shallow keel, tapering to a sharp point | |
| Arrangement | Composite, whorled on a single receptacle | |
| Persistence | Resists shatter | |
| Fragrance | Typical chrysanthemum | |
| Reproductive organs: | | |
| Stamen, anthers | 200 or more | |
| Pollen | Abundant to none (functional sterility | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 38″ when grown single stem with 2–3 long day weeks and total crop time of 11–12 weeks as defined in the timetables of Yoder Brothers, Inc., Barberton, Ohio, for the recommended seasons of the year. | |
| Spread | None when grown single stem to slight when pinched | |
| Foliage: | | |
| Top side | Dark green, 7.5GY3/4 | |
| Size | 6¾″ long, 4¼″ wide | |
| Quantity | Numerous | |
| Shape | Spatulate lobed | |
| Texture | Coarse | |
| Ribs and veins | Prominent | |
| Edge | Moderately indented | |
| Serration | Coarse | |
| Under side | Light green, 7.5GY5/4 | |
| Stipules | Prominent | |

We claim:

1. A new and distinct cultivar of chrysanthemum characterized particularly as to its uniqueness when compared to the parent cultivar Dazzler by its more intense red-bronze flower color and better color retention in high light, high temperature periods.

No references cited.

ROBERT E. BAGWILL, Primary Examiner